US 8,378,837 B2

(12) United States Patent
Wang et al.

(10) Patent No.: US 8,378,837 B2
(45) Date of Patent: Feb. 19, 2013

(54) OCCLUSION DETECTION SYSTEM

(75) Inventors: YiFei Wang, Singapore (SG); Chang Liu, Singapore (SG); See Hai Ng, Singapore (SG)

(73) Assignee: Hospira, Inc., Lake Forest, IL (US)

( * ) Notice: Subject to any disclaimer, the term of this patent is extended or adjusted under 35 U.S.C. 154(b) by 310 days.

(21) Appl. No.: 12/707,774

(22) Filed: Feb. 18, 2010

(65) Prior Publication Data

US 2010/0214110 A1    Aug. 26, 2010

Related U.S. Application Data

(60) Provisional application No. 61/154,033, filed on Feb. 20, 2009.

(51) Int. Cl.
*G08B 21/00* (2006.01)
(52) U.S. Cl. .................................. 340/665; 340/511
(58) Field of Classification Search .............. 604/151, 604/67, 122; 340/665, 511
See application file for complete search history.

(56) References Cited

U.S. PATENT DOCUMENTS

| | | |
|---|---|---|
| 4,526,574 A | 7/1985 | Pekkarinen |
| 4,863,425 A | 9/1989 | Slate et al. |
| 4,959,050 A | 9/1990 | Bobo, Jr. |
| 4,979,940 A | 12/1990 | Bobo, Jr. et al. |
| 5,096,385 A | 3/1992 | Georgi et al. |
| 5,103,211 A | 4/1992 | Daoud et al. |
| 5,116,203 A | 5/1992 | Natwick et al. |
| 5,213,573 A | 5/1993 | Sorich et al. |
| 5,242,408 A | 9/1993 | Jhuboo et al. |
| 5,254,096 A | 10/1993 | Rondelet et al. |
| 5,292,306 A | 3/1994 | Wynkoop et al. |
| 5,295,967 A | 3/1994 | Rondelet et al. |
| 5,328,460 A * | 7/1994 | Lord et al. .................. 604/67 |
| 5,695,473 A | 12/1997 | Olsen |
| 5,827,223 A | 10/1998 | Butterfield |
| 5,935,106 A | 8/1999 | Olsen |
| 5,989,222 A | 11/1999 | Cole et al. |
| 6,358,225 B1 | 3/2002 | Butterfield |
| 6,485,465 B2 | 11/2002 | Moberg et al. |
| 6,497,680 B1 | 12/2002 | Holst et al. |
| 6,585,675 B1 | 7/2003 | O'Mahony et al. |
| 6,648,861 B2 | 11/2003 | Platt et al. |
| 6,659,980 B2 | 12/2003 | Moberg et al. |
| 6,786,885 B2 | 9/2004 | Hochman et al. |

(Continued)

FOREIGN PATENT DOCUMENTS

| | | |
|---|---|---|
| EP | 319275 A1 | 1/1993 |
| EP | 335385 A2 | 10/1993 |

(Continued)

*Primary Examiner* — Hai Phan
*Assistant Examiner* — Kaleria Knox
(74) *Attorney, Agent, or Firm* — Michael R. Crabb

(57) ABSTRACT

A method of monitoring pressure inside a fluid line and a system for implementing the method. The method is applicable to syringe pump systems. The method includes the steps of measuring a force value caused by a pressure inside the fluid line; collecting the measured force values during at least two consecutive moving time windows; calculating a slope of a best-fit line within each time window; calculating a slope difference of the slopes of the best-fit lines; comparing the slope difference with a pre-determined threshold gradient value; defining a baseline force as the detected force value when the slope difference is equal to the threshold gradient value; determining a relative force value by subtracting the baseline force from the detected force value; and, triggering an alarm if the relative force is greater than a pre-defined threshold force.

18 Claims, 8 Drawing Sheets

U.S. PATENT DOCUMENTS

| | | |
|---|---|---|
| 6,887,216 B2 | 5/2005 | Hochman et al. |
| 6,942,636 B2 | 9/2005 | Holst et al. |
| 6,986,753 B2 | 1/2006 | Bui |
| 7,092,797 B2 | 8/2006 | Gaines et al. |
| 7,402,154 B2 | 7/2008 | Holst et al. |
| 7,407,489 B2 | 8/2008 | Holst et al. |
| 7,447,566 B2 | 11/2008 | Knauper et al. |
| 7,452,190 B2 | 11/2008 | Bouton et al. |
| 2003/0073954 A1 | 4/2003 | Moberg et al. |
| 2004/0030277 A1 | 2/2004 | O'Mahony et al. |
| 2004/0073161 A1* | 4/2004 | Tachibana ............... 604/67 |
| 2005/0096593 A1* | 5/2005 | Pope et al. ............. 604/122 |
| 2006/0135940 A1 | 6/2006 | Joshi |
| 2006/0224181 A1 | 10/2006 | McEwen et al. |
| 2007/0060874 A1 | 3/2007 | Nesbitt et al. |
| 2007/0270747 A1 | 11/2007 | Remde |
| 2007/0274843 A1 | 11/2007 | Vanderveen et al. |
| 2008/0221521 A1 | 9/2008 | Getz et al. |
| 2008/0221522 A1* | 9/2008 | Moberg et al. ............. 604/151 |

FOREIGN PATENT DOCUMENTS

| | | |
|---|---|---|
| EP | 429866 A1 | 5/1994 |
| EP | 431310 A1 | 1/1996 |
| EP | 589439 A2 | 8/1998 |
| JP | 07289638 A | 11/1995 |
| JP | 2003038642 A | 2/2003 |
| WO | 9304284 A1 | 3/1993 |
| WO | 2005065146 A2 | 7/2005 |
| WO | 2007033025 A2 | 3/2007 |
| WO | 2007035567 A2 | 3/2007 |

* cited by examiner

OCCLUSION DETECTION SYSTEM

CROSS REFERENCE TO RELATED APPLICATIONS

This application claims priority based upon U.S. Provisional Patent Application Ser. No. 61/154,033 filed on Feb. 20, 2009.

FEDERALLY SPONSORED RESEARCH OR DEVELOPMENT

Not Applicable.

TECHNICAL FIELD

The present invention generally relates to a method for detecting occlusions. More particularly, the present invention relates to a software algorithm that detects occlusions in the fluid lines of a syringe pump system.

BACKGROUND

Modern medical devices, including medical pumps, are increasingly being controlled by microprocessor based systems to deliver fluids, solutions, medications, and drugs to patients. Different types of medical pump systems are used depending on factors such as the dosage of fluid to be delivered, the rate of fluid delivery, the duration, and the volume of a fluid to be infused into a patient.

One example of a medical pump system used to gradually deliver small amounts of fluid to patients is a syringe pump. A typical syringe pump system includes a syringe with a plunger mounted to a housing, a motor, a pump mechanism, a pump mechanism controller, a user interface, and an alarm. The pump mechanism exerts force on the syringe plunger, and forces fluid out of the syringe into fluid lines leading to the patient. The pump mechanism includes anti-free flow claws, and a force-detecting sensor, such as a loadcell sensor.

One concern associated with using syringe pump systems is that an occlusion may occur in any of the fluid lines attached to the pump. An occlusion will cause under-delivery of the fluid to the patient, and, at the same time, pressure will build up inside the syringe and fluid lines. The built-up pressure will cause a significant bolus of fluid to be expelled through the line after the occlusion is relieved. Therefore, it is essential that the syringe pump include an occlusion detecting mechanism. One example of an occlusion detecting mechanism may be a syringe pump mechanism controller including a sensor that detects force inside the fluid lines, means for monitoring the sensor readings, and an alarm that signals to the user when a certain threshold force or pressure level has been exceeded.

One method of occlusion detection is to calculate the force on the sensor due to fluid pressure: $F_{pressure}$. In a typical syringe pump system, as shown in FIGS. 1 and 2, the following relationships are established:

$$F_{loadcell} = F_{claws} + F_{stiction} + F_{pressure} \Rightarrow F_{pressure} = F_{loadcell} - F_{claws} - F_{stiction}$$

Where $F_{loadcell}$ is the total force sensed by the loadcell. $F_{claws}$ is the portion of the total force caused by the anti-free flow claws, and $F_{stiction}$ is the portion of the total force caused by stiction. The pressure of the fluid flow in the line, $P_{liquid}$, is calculated according to the formula $$\Rightarrow P_{liquid} = \frac{F_{pressure}}{A_{syringe}}$$

$$\text{where } A_{syringe} = \pi \times \left(\frac{ID_{syringe}}{2}\right)^2$$

Where $A_{syringe}$ is the area of the syringe and $ID_{syringe}$ is the internal diameter of the syringe.

However, there are variations in stiction caused by the rubber tip of the plunger, and varying tolerances in the force caused by the anti-free flow claws. Therefore, $F_{pressure}$ typically cannot be used as the single parameter to trigger the pressure alarm because there would be too many false alarms. Accordingly, there is a need for a method of monitoring $F_{pressure}$ that also allows for variations in stiction and spring force in the anti-free flow claws to avoid triggering false alarms.

SUMMARY OF THE INVENTION

The present invention generally provides an improved method of detecting occlusions in the fluid lines of a medical infusion system, and a computer software product that performs the method. The improved method offers increased sensitivity and accuracy, without a corresponding increase in false alarms.

According to one embodiment, a detected force value caused by pressure inside a fluid line is collected. The detected force values are collected during at least two consecutive moving time windows. The slope of a best-fit line for the detected force values is calculated within each time window. In one embodiment, the best-fit line is determined by a least squares method. A slope difference of the slopes of the best-fit lines is then calculated. The slope difference is then compared with a pre-determined threshold gradient value. A baseline force is defined as the measured force value when the slope difference is equal to the threshold gradient value. A relative force value is determined by subtracting the baseline force from the detected for value. An alarm is triggered if the relative force is greater than a pre-defined threshold force.

According to another embodiment, the system comprises a syringe pump, a syringe, a processor, and a loadcell sensor operatively connected to the syringe. The system performs calculations using at least two consecutive moving time windows to process measured force values detected by the loadcell sensor. The system further: calculates the slope of a best-fit line within each time window, calculates a slope difference of the slopes of the best-fit lines, selects a threshold gradient value based on the size of the syringe; compares the slope difference to the threshold gradient value, defines a baseline force value as the measured force value when the slope difference is equal to the threshold gradient value, compares the measured force value with the baseline force value to calculate a relative force value, and triggers an alarm if the relative force value exceeds a pre-determined threshold force value.

According to another embodiment, the measured force value is converted to a pressure value. The pressure is compared to a pre-determined occlusion pressure level, and an occlusion alarm is triggered if the pressure value is greater than the threshold value.

According to another embodiment, the pump mechanism controller automatically stops the pump motor when pressure inside the fluid lines reaches the pre-determined occlusion pressure level.

Other features and advantages of the invention will be apparent from the following specification taken in conjunction with the following drawings.

BRIEF DESCRIPTION OF THE DRAWINGS

To understand the present invention, it will now be described by way of example, with reference to the accompanying drawings in which.

DETAILED DESCRIPTION

Figure 1:
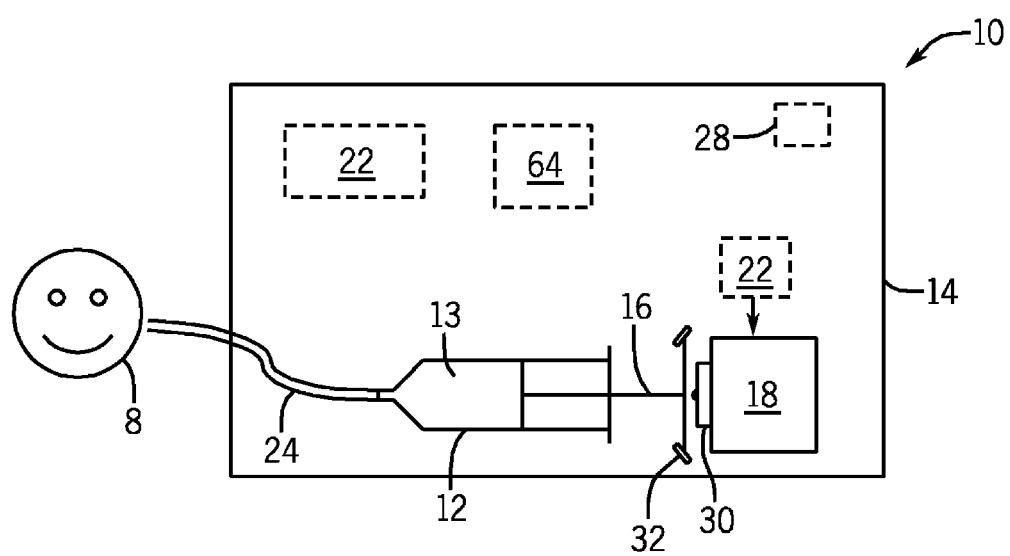
FIG. 1 is a schematic block diagram of an exemplary syringe pump system.

While this invention is susceptible of embodiments in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

Referring now to the Figures, and specifically to FIG. 1, there is shown one embodiment of a syringe pump system 10 that may be used to deliver medications to a patient 8. This embodiment of the syringe pump system 10 includes a syringe 12 holding a fluid medication 13, a housing 14, a plunger 16, a pump mechanism 18, a pump mechanism controller 20, a user interface display 22, and a fluid line 24 leading from the pump system 10 to the patient 8. The syringe pump system 10 may further include a processor 64, a communications port 28, a sensor 30 and anti-free flow claws 32. In one embodiment, the sensor 30 may be a loadcell sensor. Loadcell sensor 30 may be located at the end of pump mechanism 18 where it contacts the plunger 16.

Figure 2:
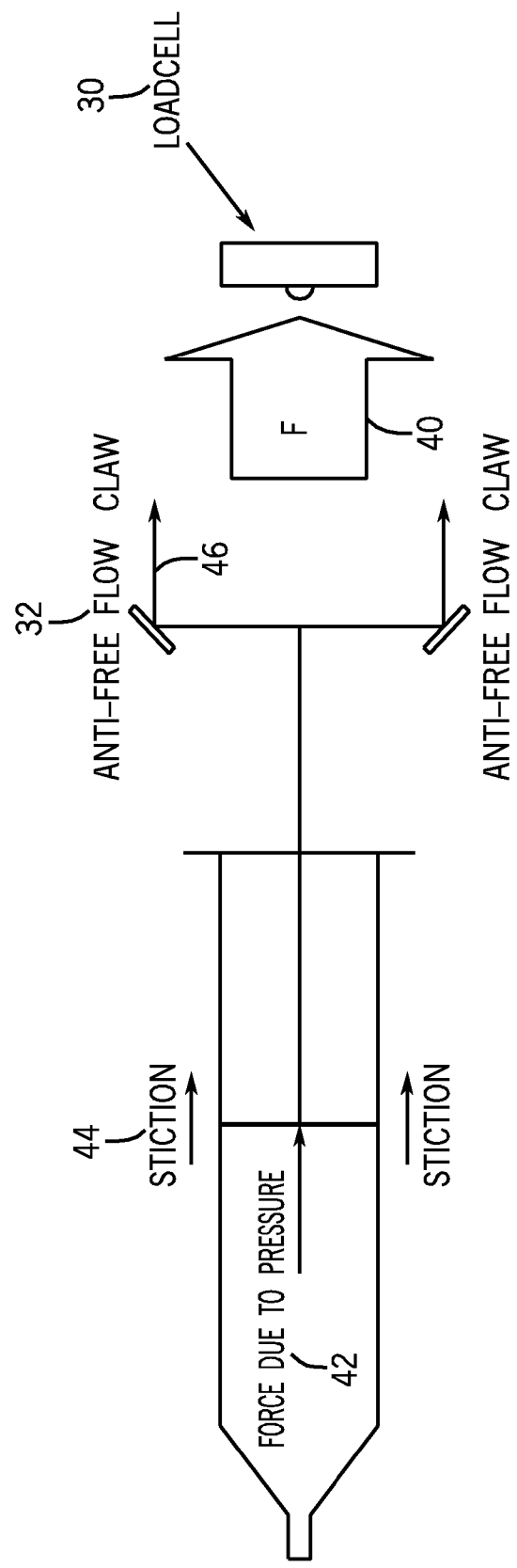
FIG. 2 is a diagram showing the forces detected by the loadcell sensor of the syringe pump system shown in FIG. 1.

As shown in the system of FIG. 2, there are at least three forces that act on a syringe loadcell sensor 30 when it is located on the end of pump mechanism 18: a fluid pressure 42, a stiction force 44, and a force 46 from the anti-free flow claws 32. The combination of these forces results in a total force 40 detected by the loadcell sensor 30. Stiction, or static friction, force 44 is the force required to overcome static cohesion between the plunger 16, fluid 13 and the walls of syringe 12. The force 46 from the anti-free flow claws 32 is a spring force caused by resistance of the anti-free-flow claws 32.

Figure 3:
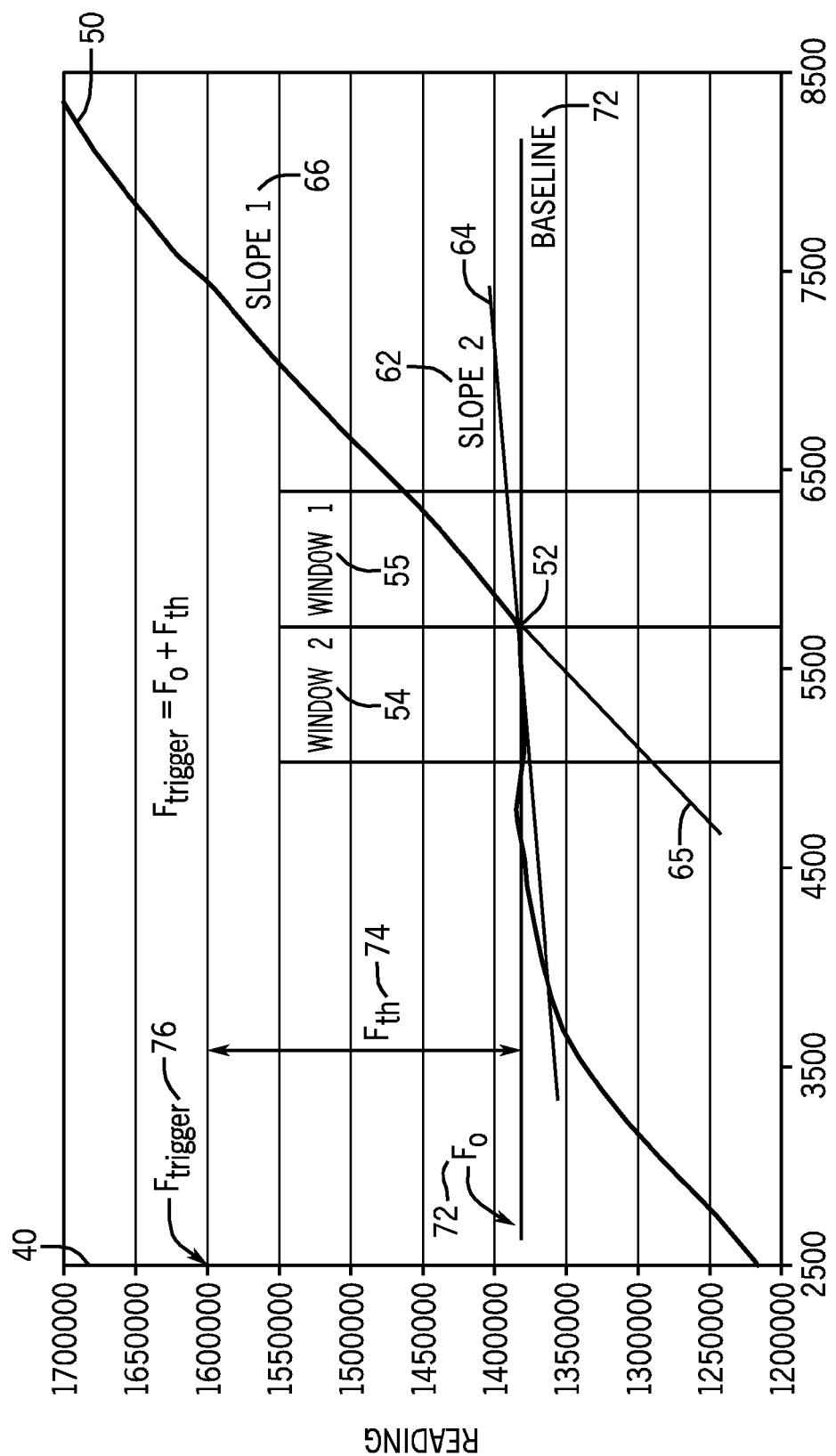
FIG. 3 is a graphical illustration of the moving windows and slope differences on a measured force versus time graph.

Referring to FIG. 3, there is shown an example of a force-time-curve 50. The force-time curve 50 is a plot of the force reading 40 measured by loadcell sensor 30 over time. A best-fit line for the force-time curve 50 may be calculated by a linear regression equation for different segments of force-time curve 50. In one embodiment, the best-fit line is determined by a least squares method. As shown in FIG. 3, the force-time curve 50 has a turning point 52. According to one embodiment, a first moving time window 54 and a second moving time window 55 are selected. In one embodiment, the moving time windows 54 and 55 are consecutive. A slope 62 of the best-fit line 64 for the force-time curve 50 in moving window 54 may be calculated. Similarly, a slope 66 of the best-fit line 65 for the force-time curve 50 within moving window 55 may also be calculated. Based on the slope 62 of the best-fit line 64 for the force-time curve 50 in the first window 54 and the slope 66 of the best-fit line 65 for the force-time curve 50 in the second window 55, a slope difference 60 may then be calculated. The slope difference 60 is calculated by subtracting the slope 62 from slope 66. Additionally, a threshold gradient 70 may also be calculated. The threshold gradient 70 is the value of slope difference 60 at the turning point 52 of force-time curve 50.

Referring again to FIG. 3, a baseline force 72 may also be established. The baseline force 72 is set as the total force 40 measured by the loadcell sensor 30 when the slope difference 60 is greater than the threshold gradient 70. A threshold force 74 may be determined based on the occlusion settings and the size of the syringe 12. Additionally, a trigger force 76 may also be calculated. The trigger force 76 is defined as the sum of the baseline force 72 and the threshold force 74. According to one embodiment, when the total force 40 detected by the loadcell sensor 30 is equal to or greater than the trigger force 76, an occlusion alarm is triggered. The pump mechanism controller 20 may also stop the pump motor 22 automatically when the occlusion alarm is triggered.

Alternately, a pressure value 80 may be calculated from total force 40. The pressure value 80 may then be compared to a pre-determined occlusion threshold pressure value 82. If the current pressure 80 is greater than the occlusion threshold pressure 82, then an occlusion alarm is triggered. Similarly, the pump mechanism controller 20 may also stop the pump motor 22 automatically when the occlusion alarm is triggered.

Figure 4:
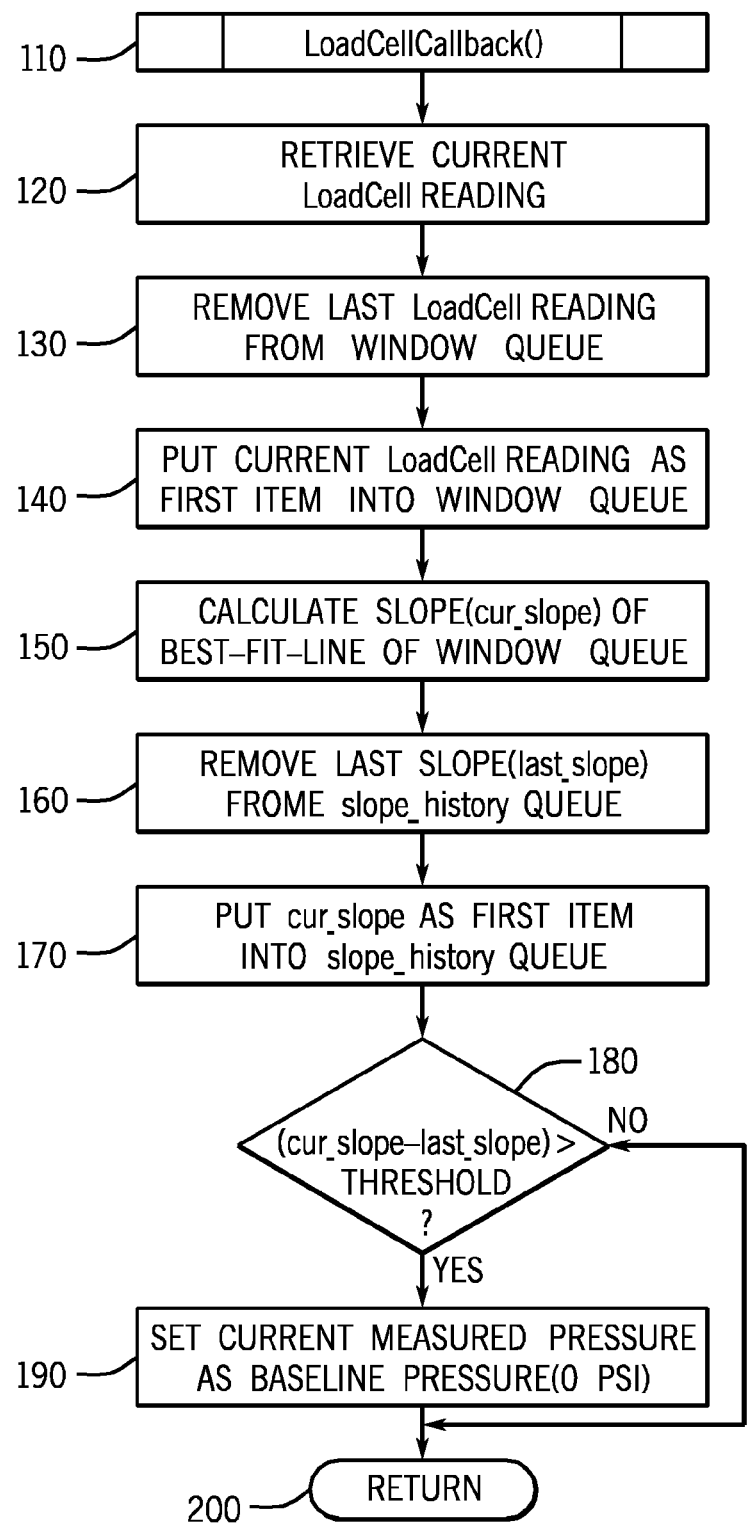
FIG. 4 illustrates how the baseline is established.

Referring now to FIG. 4, there is shown a flowchart illustrating the steps taken to establish the baseline force 72 according to one embodiment. A total force reading 40, as measured by the loadcell sensor 30 is sampled every 100 milliseconds. Multiple loadcell force readings 40 are stored in a Window Queue 112. The loadcell force readings 40 are stored in reverse chronological order, i.e., the most recent force reading is stored in a first position of the queue, and the oldest force reading is stored in a last position of the queue. Slope values 62, 66 are calculated and stored in a Slope History Queue 114. Slope values are also stored in reverse chronological order in the Slope History Queue 114.

In step 110, the most recent loadcell force 40 reading is recalled from Window Queue 112. A current loadcell force 40 reading is retrieved in step 120, and the last (oldest) loadcell force reading 40 is removed from the last position of Window Queue 112 in step 130. In step 140, the current loadcell force 40 reading is put into the first position of Window Queue 112. A current slope value (cur_slope) of the best-fit line for the force readings stored in Window Queue 112 is calculated in step 150. In step 160, a last slope value (last_slope) is removed from a last position in Slope History Queue 114, and in step 170, the current slope value (cur_slope) is added to a first position of Slope History Queue 114. Then, in step 180, the slope difference 60 between the current slope value (cur_slope) and the last slope value (last_slope) is calculated, and compared to the threshold gradient 70. If the slope difference 60 is greater than the threshold gradient 70, the calculated pressure corresponding to the current measured force is set as the baseline pressure 82 (0 psi) in step 190. In step 200, the process starting with step 110, is repeated for each pair of moving time windows. If the slope difference 60 is not greater than the threshold gradient 70, step 190 is not performed, and the process is repeated beginning with step 110 for the next total force reading 40.

Figure 5:
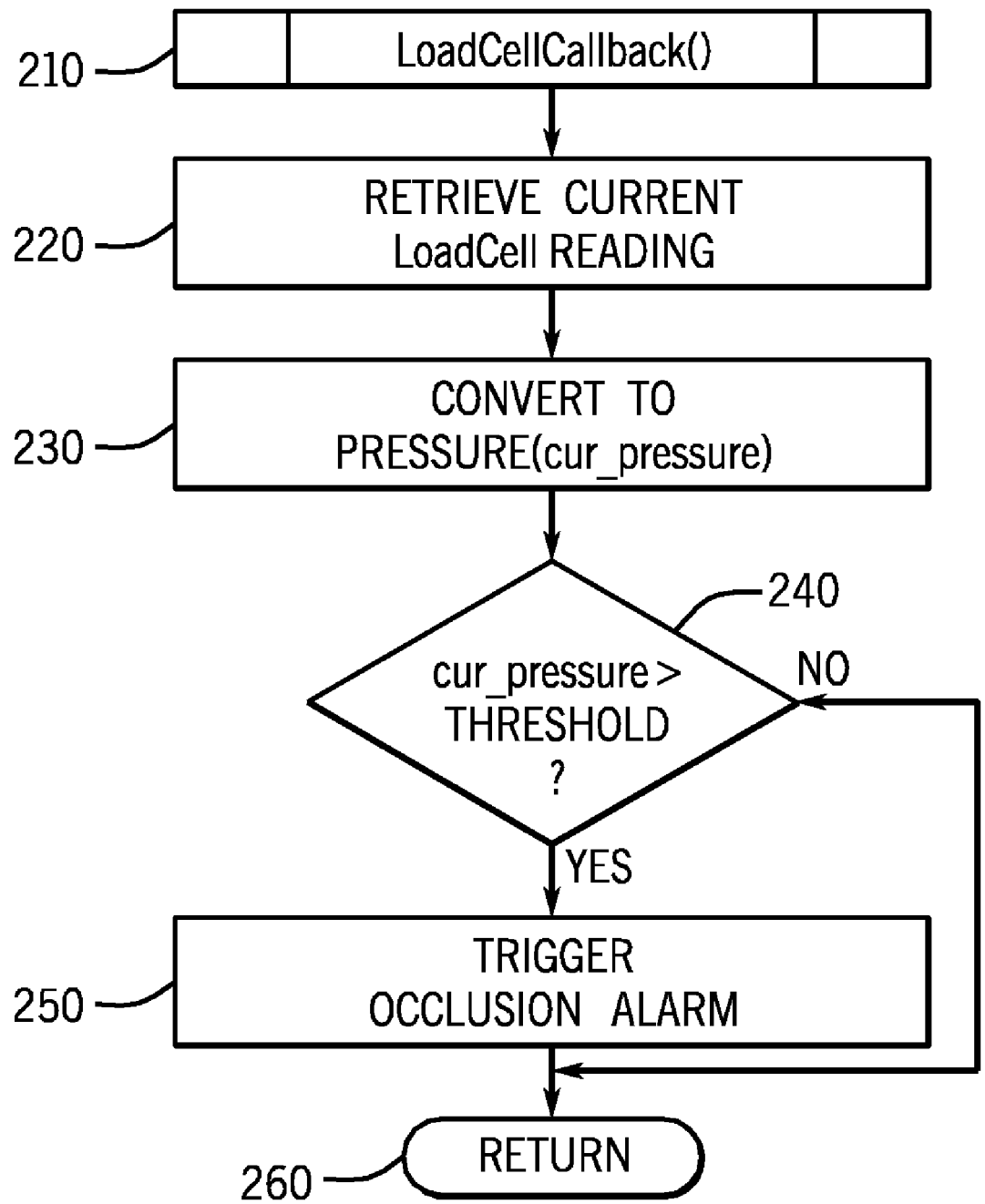
FIG. 5 illustrates how an occlusion is detected according to one method of the present invention.

FIG. 5 is a flowchart illustrating the steps for detecting occlusions according to one embodiment. Specifically, after detecting the turning point 52 and establishing the baseline force 72, the following steps shown in FIG. 5 monitor the current pressure 80. The total force readings 40 measured by the loadcell sensor 30 are stored in a Window Queue 112. Starting with step 210, the most recent loadcell force reading 40 is recalled from Window Queue 112. Then, a current loadcell force reading 40 is retrieved in step 220. The current loadcell force reading 40 is converted to a current pressure value 80 in step 230. In step 240, the current pressure value 80 is compared to an occlusion threshold pressure 82. If the current pressure value 80 is greater than the occlusion threshold pressure 82, an occlusion alarm is triggered. If the current pressure value 80 is less than the occlusion threshold pressure 82, the process repeats, starting with step 210.

Figure 6:
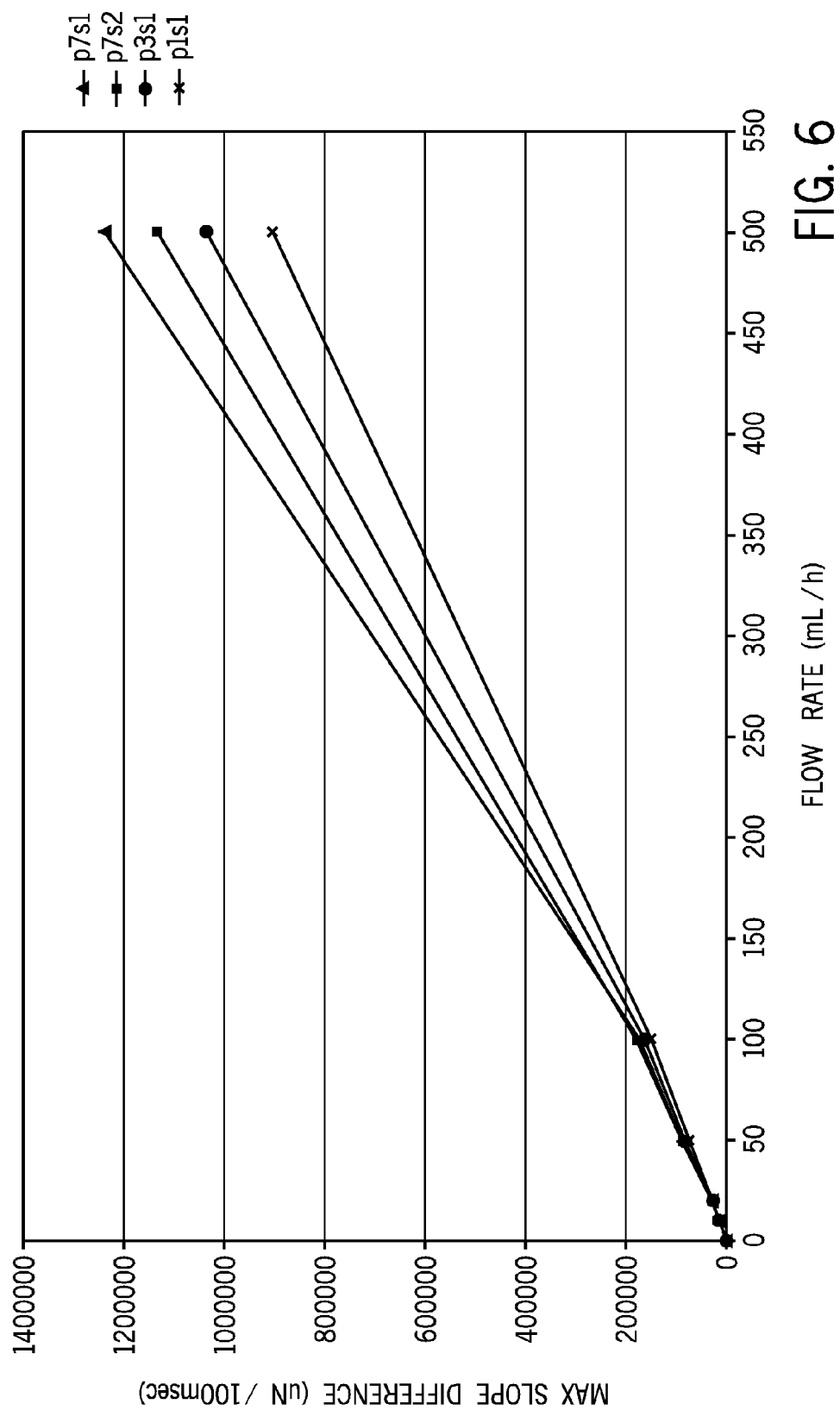
FIG. 6 is a plot of maximum slope difference versus flow rate.

FIG. 6 is a plot of the maximum observed slope differences 61 for a 30 cc syringe running at different flow rates 86. As is shown in FIG. 6, as the flow rate increases, a maximum slope difference 61 also increases, according to approximately a 1/x ratio. It has been observed that doubling the flow rate 86 doubles the maximum slope difference 61. In one embodiment, the threshold gradient 70 is set as 50% of the maximum observed slope difference 61 at a particular flow rate 86. This threshold gradient value accounts for variation in the maximum slope difference due to differences across pumps and syringes.

Figure 7:
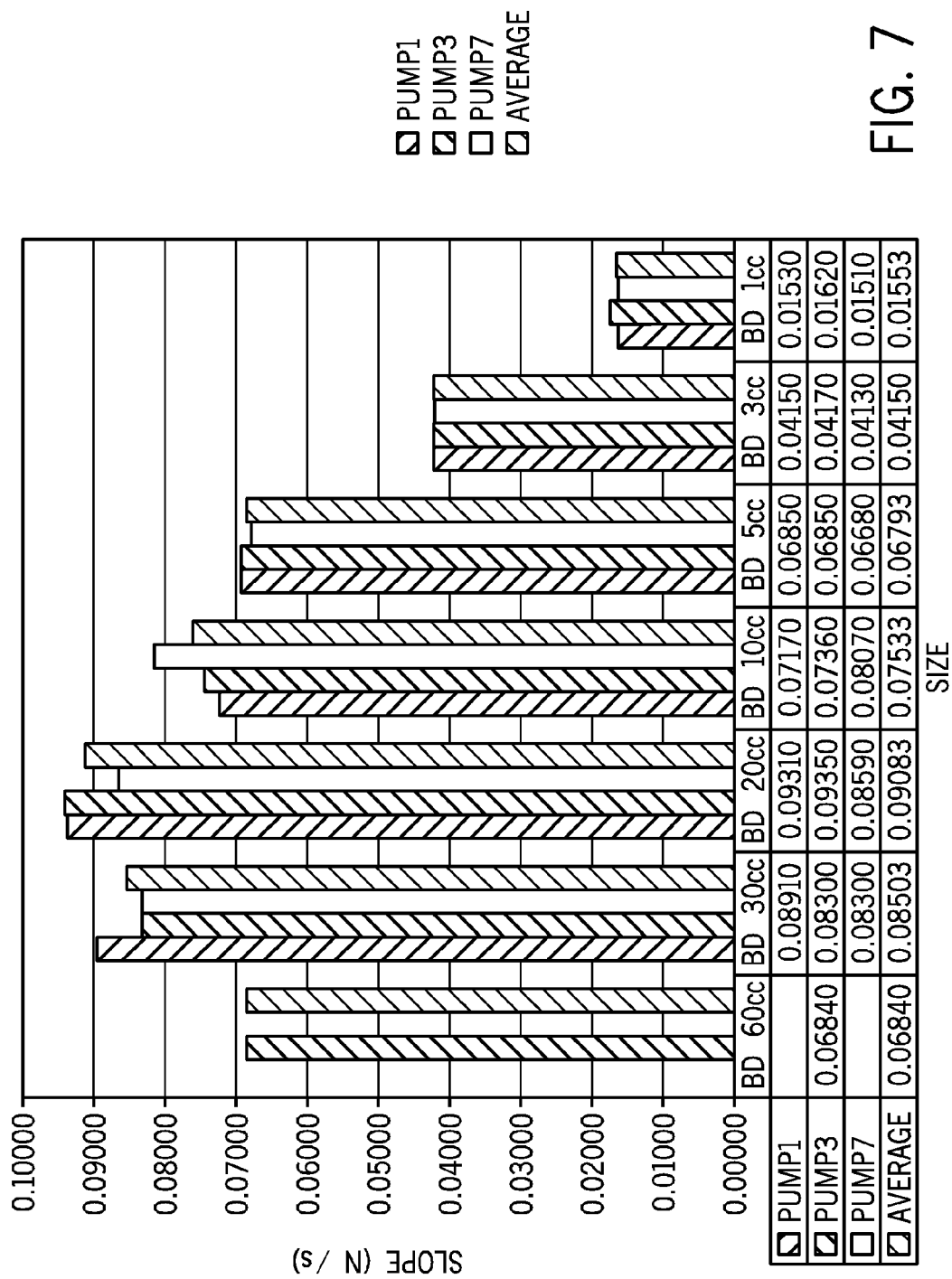
FIG. 7 shows how the threshold gradient changes with respect to syringe size.

FIG. 7 is a bar graph showing how the threshold gradient 70 changes in relation to the size of syringe 12. As shown in FIG. 7, the change in threshold gradient 70 in relation to syringe size is not linear. Thus, the value at which the threshold gradient 70 should be set is different for different syringe sizes. To account for such different threshold gradients 70, the processor 64 of the system 10 may include a lookup table 90, and different threshold gradient values corresponding to different syringe sizes may be stored in the lookup table 90. In one embodiment the processor 64 sets the threshold gradient 70 based on the size of syringe 12. Syringe size may be input by the user or automatically detected by the processor 64. One example of lookup table 90 is Table 1, below:

TABLE 1

Formulation for setting the threshold gradient for different syringe sizes

| | Syringe Size | | | | | |
|---|---|---|---|---|---|---|
| 60 cc | 30 cc | 20 cc | 10 cc | 5 cc | 3 cc | 1 cc |
| % of gradient threshold 80% | 100% | 107% | 89% | 80% | 49% | 18% |

Similarly, the size of the moving windows 54 and 55 must be selected. The accuracy of turning point 52 corresponds to the size of windows 54, 55. Accordingly, if the windows 54 and 55 are small, the possibility of false alarms may increase because turning point 54 will be subject to more noise and may be less accurate. Conversely, if the windows 54 and 55 are large, the turning point 52 will be more accurate, but the time required to establish the baseline 72 will increase. This can lead to an increased risk that the preset pressure triggering level 82 or force triggering level 76 will be reached before baseline 72 can be calculated. Since an alarm may not be triggered before the baseline 72 is established, the occlusion could go undetected. Thus, an optimal window size 87 produces the most accurate turning point 52, but the time taken to establish turning point 52 will be relatively long. A minimum window size 88 is the smallest window required in order to find the turning point 52.

Figure 8:
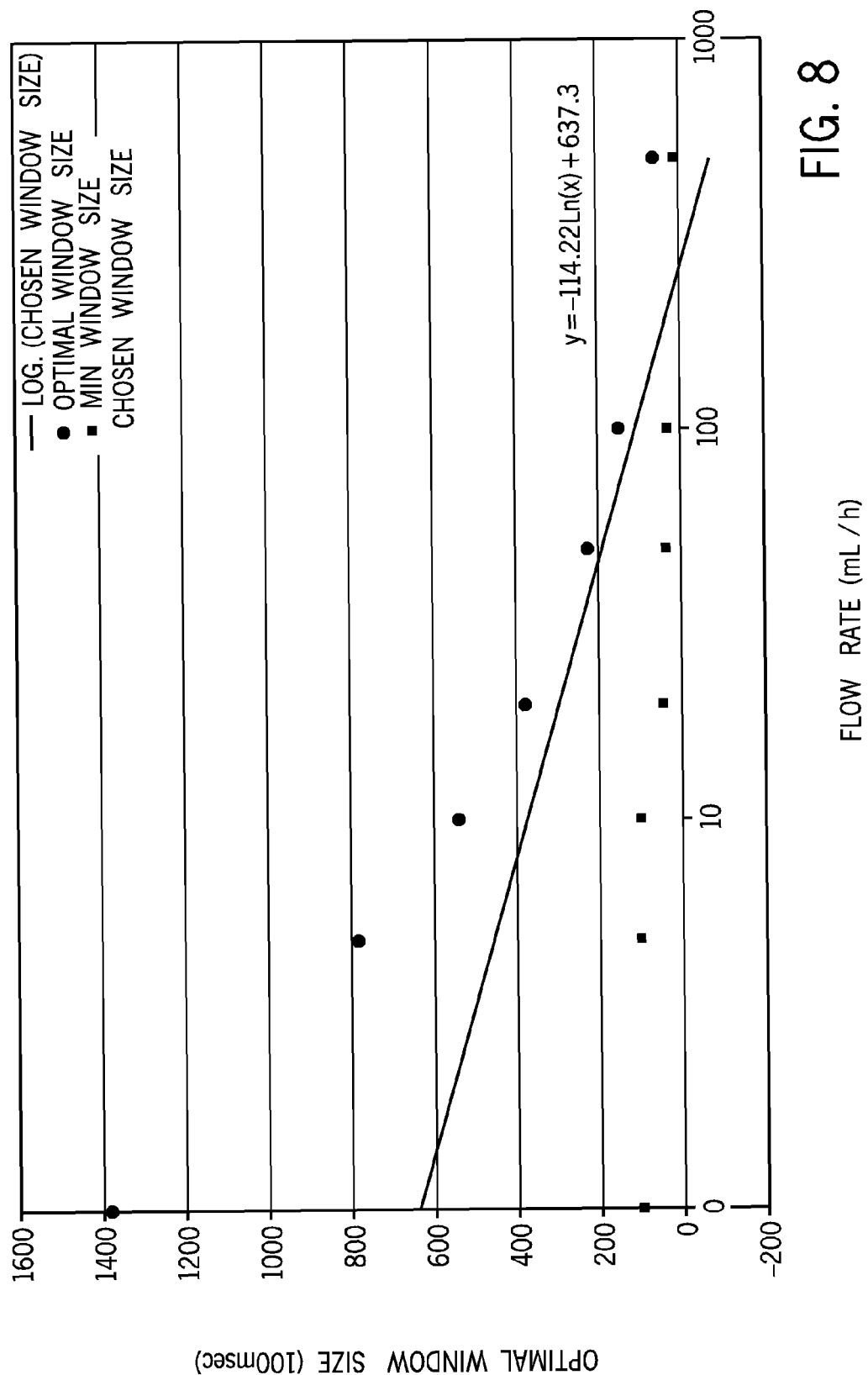
FIG. 8 shows the relationship between window size and flow rates.

Referring now to FIG. 8, there is shown a plot of optimal window size 87 versus flow rate 86. As is shown in FIG. 8, the optimal window size 87 decreases as the flow rate 86 increases. According to one embodiment, the selected window size 89 is calculated by finding the best-fit line for an average between the optimal window size 87 and the minimum window size 88. In one embodiment, the best-fit line is determined by a least squares method. The selected window size 89 may be a compromise between processing time for calculating the baseline 72 and the accuracy of determining the turning point 52.

According to one embodiment, the processor 64 determines the size of the moving windows 54 and 55 for a particular flow rate 86. The processor 64 calculates the turning point 52 based on the threshold gradient value 70 selected for the particular size syringe 12 according to the look-up table 90. The processor 64 stores the measured force values 70 detected by the loadcell sensor 30. The processor 64 then calculates a slope difference 60 of the slope of the best-fit lines 64, 65 within each moving window 54, 55. The processor 64 compares the slope difference 60 to the threshold gradient value 70. The processor 64 sets the baseline force 72 as the measured force value 40 at the point when the slope difference 60 is greater than the threshold gradient value 70. After the baseline force 72 is set, the processor 64 compares the measured force value 70 to the baseline force 72. The processor 64 triggers an alarm if the measured force value 70 is greater than the trigger force 76 (trigger force 76 is calculated as the threshold force 74 plus the baseline force 72). Threshold force 74 is calculated based on the pressure occlusion settings for a particular syringe size 12.

Several alternative embodiments and examples have been described and illustrated herein. A person of ordinary skill in the art would appreciate the features of the individual embodiments, and the possible combinations and variations of the components. A person of ordinary skill in the art would further appreciate that any of the embodiments could be provided in any combination with the other embodiments disclosed herein. Additionally, the terms "first," "second," "third," and "fourth" as used herein are intended for illustrative purposes only and do not limit the embodiments in any way. Further, the term "plurality" as used herein indicates any number greater than one, either disjunctively or conjunctively, as necessary, up to an infinite number. Additionally, the term "having" as used herein in both the disclosure and claims, is utilized in an open-ended manner.

It will be understood that the invention may be embodied in other specific forms without departing from the spirit or central characteristics thereof. The present examples and embodiments, therefore, are to be considered in all respects as illustrative and not restrictive, and the invention is not to be limited to the details given herein. Accordingly, while the specific embodiments have been illustrated and described, numerous modifications come to mind without significantly departing from the invention.

We claim:

1. A method of monitoring pressure inside a fluid line, comprising the steps of:
   measuring a force value caused by a pressure inside the fluid line;
   collecting and storing force values during at least two consecutive time windows;

calculating a slope of a best-fit line based upon the force values within each time window;

calculating a slope difference between the slopes of the best-fit lines;

comparing the slope difference with a pre-determined threshold gradient value;

defining a baseline force as the measured force value when the slope difference is at least equal to the threshold gradient value;

calculating a relative force value by subtracting the baseline force from the measured force value; and, initiating an alarm if the relative force value is greater than a value of the pre-defined threshold force value.

2. The method of claim 1 wherein the best-fit line is obtained by a linear regression equation.

3. The method of claim 1 wherein the threshold gradient value is defined as the slope difference equal to 50% of a maximum slope difference at a selected flow rate.

4. The method of claim 1 wherein the threshold gradient value is determined based on a size of a syringe connected to the fluid line.

5. The method of claim 4 wherein for a 60 cc syringe, the threshold gradient value is equal to 80% of a maximum slope difference at a selected flow rate.

6. The method of claim 4 wherein for a 30 cc syringe, the threshold gradient value is equal to 100% of a maximum slope difference at a selected flow rate.

7. The method of claim 4 wherein for a 20 cc syringe, the threshold gradient value is equal to 107% of a maximum slope difference at a selected flow rate.

8. The method of claim 4 wherein for a 10 cc syringe, the threshold gradient value is equal to 89% of a maximum slope difference at a selected flow rate.

9. The method of claim 4 wherein for a 5 cc syringe, the threshold gradient value is equal to 80% of a maximum slope difference at a selected flow rate.

10. The method of claim 4 wherein for a 3 cc syringe, the threshold gradient value is equal to 49% of a maximum slope difference at a selected flow rate.

11. The method of claim 4 wherein for a 1 cc syringe, the threshold gradient value is equal to 18% of a maximum slope difference at a selected flow rate.

12. The method of claim 1 wherein a window size for a flow rate is selected based on a best-fit line for an average between an optimal and a minimum window size for a range of flow rates.

13. A method of monitoring pressure inside a fluid line, comprising the steps of:

measuring a force value caused by a pressure inside the fluid line;

collecting and storing force values during at least two consecutive time windows;

calculating a slope of a best-fit line based upon the force values within each time window, wherein the best-fit line is obtained by a linear regression equation;

calculating a slope difference between the slopes of the best-fit lines;

comparing the slope difference with a pre-determined threshold gradient value;

defining a baseline force value as the measured force value when the slope difference is at least equal to the threshold gradient value;

calculating a baseline pressure value corresponding to the baseline force value;

calculating a current pressure value from the measured force value;

calculating a relative pressure value by subtracting the baseline pressure value from the current pressure value;

comparing the relative pressure value to a pre-determined pressure threshold value;

and initiating an alarm if the current pressure value is greater than the pre-determined pressure threshold value.

14. The method of claim 13, wherein the alarm includes a control signal.

15. An occlusion detection system comprising:

a pump having a sensor operatively connected to a fluid line for delivering fluid for the pump, and a processor, wherein the processor:

uses at least two consecutive moving time windows to process measured force values detected by the sensor;

calculates a slope of a best-fit line for the measured force values collected within each time window, calculates a slope difference of the slopes of the best-fit lines;

selects a threshold gradient value based on the size of the syringe;

compares the slope difference to the threshold gradient value;

defines a baseline force value as the measured force value when the slope difference is equal to the threshold gradient value;

compares the measured force value with the baseline force value to calculate a relative force value; and, initiates an alarm if the relative force value exceeds a pre-determined threshold force value.

16. The system of claim 15 wherein the threshold force value is determined based on an internal diameter of a portion of the fluid line defined by a syringe.

17. The system of claim 15 wherein the sensor is a loadcell sensor.

18. The system of claim 15, wherein a current pressure value is calculated corresponding to the measured force value; the current pressure value is compared to a pre-determined pressure threshold value; and an alarm is initiated if the current pressure value exceeds the pre-determined threshold value.

* * * * *